United States Patent [19]

Ams et al.

[11] Patent Number: 4,782,386

[45] Date of Patent: Nov. 1, 1988

[54] VIDEO ENDOSCOPE WITH A LIGHT SOURCE OPERABLE IN A CONTINUOUS OR STROBOSCOPIC MODE

[75] Inventors: Felix Ams, Kaempfelbach; Reiner Hoffmann, Illingen; Peter Jaggy, Oetisheim, all of Fed. Rep. of Germany

[73] Assignee: Richard Wolf GmbH, Fed. Rep. of Germany

[21] Appl. No.: 21,809

[22] Filed: Mar. 4, 1987

[30] Foreign Application Priority Data

Mar. 8, 1986 [DE] Fed. Rep. of Germany ....... 3607767

[51] Int. Cl.$^4$ ............................................. H04H 7/18
[52] U.S. Cl. ..................................... 358/93; 358/101; 358/106; 356/23; 128/6
[58] Field of Search ............... 358/98, 101, 108, 93, 358/106; 128/4, 6; 356/23; 258/211, 205

[56] References Cited

U.S. PATENT DOCUMENTS

| | | | |
|---|---|---|---|
| 2,244,687 | 6/1941 | Goldsmith et al. | 352/49 |
| 2,244,688 | 6/1941 | Goldsmith et al. | 352/49 |
| 2,343,971 | 3/1944 | Goldsmith | 358/41 |
| 2,867,209 | 1/1959 | Fouses et al. | 128/6 |
| 3,244,167 | 4/1966 | Ferris et al. | 128/6 |
| 4,175,545 | 11/1979 | Termanini | 128/666 |
| 4,219,014 | 8/1980 | Oshiro et al. | 128/6 |
| 4,240,110 | 12/1980 | Henry | 358/106 |
| 4,318,081 | 3/1982 | Yoshida | 358/101 |
| 4,319,269 | 3/1982 | Kajiurn et al. | 358/106 |
| 4,349,014 | 9/1982 | Takamatsu | 128/6 |
| 4,380,026 | 4/1983 | Kubota | 356/23 |
| 4,384,775 | 5/1983 | Hosoda | 354/62 |
| 4,416,524 | 11/1983 | Takayama | 354/31 |
| 4,423,436 | 12/1983 | Kimura | 358/98 |
| 4,446,481 | 5/1984 | Edamatsu et al. | 358/106 |
| 4,535,758 | 8/1985 | Longacre, Jr. | 358/98 |
| 4,562,831 | 1/1986 | Murakoshi et al. | 358/98 |
| 4,599,630 | 8/1971 | Sato et al. | 128/6 |
| 4,621,284 | 11/1986 | Nihioka et al. | 128/6 |
| 4,636,849 | 1/1987 | Wada et al. | 358/106 |
| 4,685,451 | 8/1987 | Ando | 128/6 |

FOREIGN PATENT DOCUMENTS

OS2014662 3/1970 Fed. Rep. of Germany .
GM7440701 12/1974 Fed. Rep. of Germany .

Primary Examiner—James J. Groody
Assistant Examiner—John K. Peng
Attorney, Agent, or Firm—Hill, Van Santen, Steadman & Simpson

[57] ABSTRACT

A video endoscope has a strobe lamp operable in a mode wherein the strobing is synchronized to a selected tone or a periodic vibration in a patient, such as from the vocal cords, and is alternatively operable in a mode wherein the strobing is so rapid so as to appear as a substantially continuous light source. In the second mode, wherein the resulting image is to be displayed by a video system, the trigger circuit for operating the lamp is supplied with the video signal so that the lamp is triggered during either the horizontal or vertical blanking interval so that triggering of the strobe lamp does not cause interference in the video picture.

24 Claims, 1 Drawing Sheet

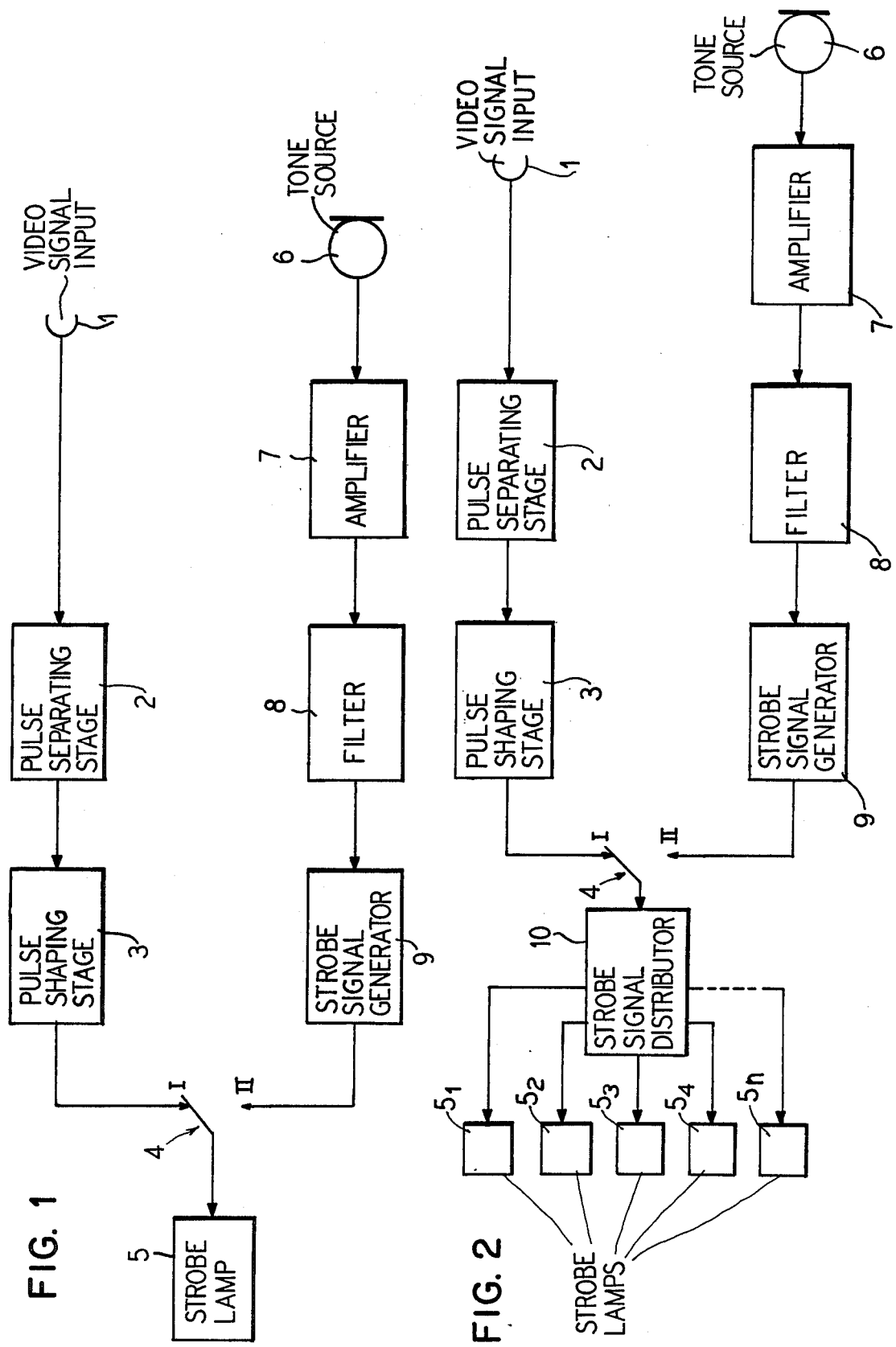

VIDEO ENDOSCOPE WITH A LIGHT SOURCE OPERABLE IN A CONTINUOUS OR STROBOSCOPIC MODE

BACKGROUND OF THE INVENTION

1. Field of the Invention

The present invention is related to a video endoscope, and in particular to a video endoscope having a strobe lamp for phase-synchronous stroboscopic illumination of an examination subject.

2. Related Application

The present application is related to the co-pending application of Reiner Hoffman and Peter Jaggy entitled "Circuit For A Flash Stroboscope For Examining Vocal Chord Functions" filed Oct. 10, 1986 and having Ser. No. 917,692, assigned to the assignee of the present application.

3. Description of the Prior Art

Video endoscopes, sometimes called video technoscopes, are optical devices used to observe the interior of an examination object through exterior openings therein, wherein the image is "seen" by an optical system, with the output of the optical system being forwarded by a video system for reproduction on the picutre screen of a monitor.

In medical applications, for example, laryngoscopy or epilaryngoscopy, such video endoscopes are used for observing internal organs of a human or animal examination subject.

Under such circumstances, the object under examination is generally illuminated with continuous light generated by a light source, the light being conducted to the examination subject by optical fibers.

Stroboscopic examination are also possible wherein a vibrating member, for example, the vocal cords, is illuminated with phase-synchronized flashes thus rendering the periodic sequences visible. Deviations from normal vibrational behavior due, for example, to organic changes, diseases, injuries or the like can be identified by this method, so that the necessary therapy can be prescribed.

Endoscopes are known which provide for changing from continuous illumination by, for example, a pilot lamp, to stroboscopic illumination by a phase-synchronously controllable strobe lamp. The endoscope described in German OS No. 20 14 662 provides a beam deflection means with which the continuous light of the pilot lamp or the strobe lamp of the electronic flash device can be alternatively supplied to the light guide.

The structural components and, more importantly, the space requirements for such endoscopes are relatively high due to the use of two different light sources.

SUMMARY OF THE INVENTION

An object of the present invention is to provide an endoscope with a single light source which can be operated as a phase-synchronous strobe lamp or a substantially continuous source of illumination.

A further object of the present invention is to provide such an endoscope, wherein triggering of the strobe lamp does not result in interference in the video picture of the examination object.

The above objects are achieved in accordance with the principles of the present invention in an endoscope having a single strobe lamp with a switch for selectively operating the strobe lamp as a phase-synchronous illumination source or as a substantially continuous illumination source. When operated as a substantially continuous illumination source, the strobe lamp is triggered so quickly that the successive flashes appear to the human eye as substantially continuous light. When operated in the substantially continuous mode, the strobe lamp is triggered during the blanking interval of the line sync pulse or vertical sync pulse for the video transmission and reproduction system. During the horizontal blanking interval, the electron beam of the picture tube returns from the end of one line to the beginning of the next line. Noise pulses caused by triggering the strobe lamp during this blanking interval cannot cause any picture interference.

During the vertical blanking interval, the electron beam returns from the lower right edge of the picture in the last line to the upper left edge of the first line in the picture. Noise pulses are not visible on the picture screen during this blanking interval either.

If triggered during the horizontal blanking interval, the strobe lamp or bulb must be triggered extremely fast, that is, with the horizontal scanning frequency. Such light pulses are imperceptible to the human eye, so that this sequence of strobe light appears as continuous light.

If triggered during the horizontal blanking interval, the strobe light sequence will be generated with a frequency of 50 Hz, which also appears to the human eye as a substantially constant continuous light, which is qualitatively equivalent to the continuous light generated by a true continuous light source, thus permitting visual examination of the observation subject.

Operation in this manner permits a conventional magnifier endoscope, for example of the type described in German Utility Model No. 74 40 701, to be used as an endoscope.

In one embodiment for controlling operation of the strobe lamp, the video signal is taken from the video system, preferably at the video camera, and is supplied to a pulse separating stage which separates the line sync pulse or the vertical sync pulse, as needed, from the incoming signal. The pulse separating stage is followed by a pulse shaping stage which generates the trigger pulse for the strobe lamp.

In another embodiment of the invention, a plurality of light flashes can be generated with a light projector or a plurality of light projectors so as to improve illumination during the blanking interval, particularly during the vertical blanking interval, which is longer. The light flashes can be simultaneously triggered or triggered in chronological succession.

A change from quasi-continuous illumination to stroboscopic illumination can be undertaken in the video endoscope in accordance with the principles of the present invention by a simple electrical switching means. For stroboscopic illumination, the strobe repetition rate can either be set manually in a known manner, or can be externally triggered dependent on the intrinsic oscillation of the observation subject.

DESCRIPTION OF THE DRAWINGS

FIG. 1 is a schematic block diagram of an apparatus for operating a strobe single lamp in a video endoscope constructed in accordance with the principles of the present invention.

FIG. 2 is a schematic block diagram of an apparatus for operating multiple strobe lamps in a video endoscope constructed in accordance with the principles of the present invention.

DESCRIPTION OF THE PREFERRED EMBODIMENTS

As shown in FIG. 1, a video signal input is taken from the video system used in connection with an endoscope. The video system may be a video pick-up, transmission, recording or playback system having a jack 1, such as at the video camera (not shown).

The remaining elements of the endoscope are also not shown in the drawings, those elements not being necessary to describe the subject matter of the present invention. The endoscope is, however, illuminated by a strobe lamp 5. Any strobe light source such as a lamp or stroboscope whose light source can be connected to the endoscope via a light guide is suitable for this purpose.

In order to separate the sync pulses from the video signal supplied at the jack 1, the signal is supplied to a pulse separating stage 2. The sync pulses which are present during the blanking interval are then supplied to a pulse shaping stage 3, for example, a trigger circuit. The pulse shaping stage 3 generates trigger pulses for the strobe lamp 5, which are supplied to the strobe lamp 5 via a selection switch 4.

In the position I, which corresponds to the "observation" operating mode, the stobe lamp 5 generates light flashes with either the horizontal scanning or frame frequency during the blanking interval, so that the observation subject is adequately illuminated without the trigger pulses for the strobe lamp 5 causing disturbing streak formation on the picture screen.

In the switch position 11, stroboscopic observation is possible in a known manner.

When the switch 4 is in position 11, the strobe lamp is operated by a signal from a strobe signal generator 9. The input signal for the strobe generator 9 is obtained from a tone source or generator 6 which may be manually variable in frequency, so that the flashing rate can be continuously varied and adapted to the desired motion sequence. External synchronization is also possible, as is preferably used in examination of the vocal cords. In this case, the tone source is a microphone, preferably a laryngophone, which picks up the voice of the patient. The signal is supplied after amplification by an amplifier 7 to a filter 8, which serves the purpose of frequency processing. By means of the filter 8, the signal having the fundamental frequency with which the stroboscope generator 9 is synchronzied is filtered out of the frequency mix. The trigger pulse is generated by the generator 9 and supplied to the strobe lamp 5 via the switch 4 thus have the same frequency as the fundamental oscillation of the vibrating subject under examination, such as the vocal cords.

As shown in FIG. 2, a plurality of light sources, such as strobe lamps $5_1 \ldots 5_n$ may be used instead of a single light source. Each of the strobe lamps $5_1 \ldots 5_n$ is connected to a strobe signal distributor 10. In the operational mode with the switch 4 in position II, the output signals from the strobe signal generator 9 are supplied to the strobe signal distributor 10. The strobe signal generator may generate a signal which is simultaneously supplied by the strobe signal generator to each of the strobe lamps $5_1 \ldots 5_n$, to cause all of those lamps to flash simultaneously. Alternatively, the strobe signal generator may generate a series of successive pulses, which are successively supplied by the strobe signal distributor 10 in a known manner one at a time to each of the strobe lamps $5_1 \ldots 5_n$, to cause the lamps to flash in rapid succession. All other elements of the embodiment of FIG. 2 operate as described above in connection with FIG. 1. When the endoscope shown in FIG. 2 is operated with the switch 4 in the position I, the strobe signal distributor simply functions as a direct connection between the output of the pulse shaping stage 3 and as many of the strobe lamps $5_1 \ldots 5_n$ as are desired to be used in that mode.

Although modifications and changes may be suggested by those skilled in the art it is the intention of the inventors to embody within the patent warrented hereon all changes and modifications as reasonably and properly come within the scope of their contribution to the art.

We claim as our invention:

1. An apparatus for operating a light source to illuminate an examination subject for use with a video system for displaying an image of said subject, said apparatus comprising:
    first means for triggering flashing of said light source at a frequency appearing as continuous illumination of said examination subject to a human observer including means for synchronizing triggering of said flashing so as to prevent interference with the video display of said image;
    second means for triggering flashing of said light source for non-continuous appearing illumination of said examination subject; and
    means connected to said light source and to said first and second means for triggering for selectively connecting one of said first or second means for triggering to said light source.

2. An apparatus as claimed in claim 1, wherein said video system has a video output signal including a horizontal blanking interval, and wherein said means for synchronizing is a means for causing triggering of said flashing of said light source during said horizontal blanking interval.

3. An apparatus as claimed in claim 2, further comprising a plurality of additional light sources and wherein said first means for triggering is a means for simultaneously triggering flashing of each of said light source and said additional light sources during said horizontal blanking interval.

4. An apparatus as claimed in claim 2, further comprising a plurality of additional light sources and wherein said first means for triggering is a means for successively chronologically triggering each of said light source and said additional light sources during said horizontal blanking interval.

5. An apparatus as claimed in claim 1, wherein said video system has a video output signal including a vertical blanking interval, and wherein said means for synchronizing is a means for causing triggering of said flashing during said vertical blanking interval.

6. An apparatus as claimed in claim 5, further comprising a plurality of additional light sources and wherein said first means for triggering is a means for simultaneously triggering each of said light source and said additional light sources during said vertical blanking interval.

7. An apparatus as claimed in claim 5, further comprising a plurality of additional light sources and wherein said first means for triggering is a means for successively chronologically triggering each of said light source and said additional light sources during said vertical blanking interval.

8. An apparatus as claimed in claim 1, wherein said examination subject is oscillating, and wherein said second means for triggering includes means for synchronizing triggering of flashing of said light in phase with the oscillation of said examination subject.

9. An apparatus as claimed in claim 8, wherein said means for synchronizing includes a tone source for generating a tone to which said triggering is synchronized.

10. An apparatus as claimed in claim 9, wherein said tone source is a tone generator with manually variable frequency control.

11. An apparatus as claimed in claim 9, wherein said tone source is a microphone arranged for picking up oscillations of said examination subject.

12. An apparatus as claimed in claim 1, wherein said light source is a strobe lamp.

13. An apparatus for operating a light source to illuminate an examination subject for use with a video system for displaying an image of said subject, said video system generating a video output signal having a blanking interval, said apparatus comprising:
  first means for triggering flashing of said light source at a frequency appearing as continuous illumination of said examination subject to a human observer including means for timing triggering of said flashing during said blanking interval thereby preventing interference with the video display of said image;
  said means for triggering flashing of said light source for non-continuous appearing illumination of said examination subject; and
  means connected to said light source and to said first and second means for triggering for selectively connecting one of said first or second means for triggering to said light source.

14. An apparatus as claimed in claim 13, wherein said blanking interval is the horizontal blanking interval.

15. An apparatus as claimed in claim 13, wherein said blanking interval is the vertical blanking interval.

16. An apparatus as claimed in claim 13, wherein said light source is a strobe lamp.

17. An apparatus for operating a light source to illuminate an examination subject for use with a video system for displaying an image of said subject, said video system generating a video output signal including sync pulses, said apparatus comprising:
  a pulse separating stage to which said video output signal is supplied, said pulse separating stage separating said sync pulses from said video output signal;
  a pulse shaping stage to which said sync pulse is from said pulse separating stage are supplied, said pulse shaping stage generating a trigger pulse for said light source coinciding with each sync pulse, said pulse shaping stage generating said trigger pulses at a frequency such that flashing of said light source appears as continuous illumination of said examination subject to a human observer;
  further means for triggering flashing of said light source for non-continuous appearing illumination of said examination subject; and
  means connected to the output of said pulse shaping stage and to said further means for triggering and to said light source for selectively connecting one of said pulse shaping stage or said further means for triggering to said light source.

18. An apparatus as claimed in claim 15, wherein said sync pulses are line sync pulses.

19. An apparatus as claimed in claim 15, wherein said sync pulses are frame sync pulses.

20. An apparatus as claimed in claim 17, wherein said light source is a strobe lamp.

21. An apparatus for operating a light source to illuminate an oscillating examination subject for use with a video display system for displaying an image of said subject, said video system generating a video output signal having sync pulses, said apparatus comprising:
  a pulse separating stage to which said video output signal is supplied, said pulse separating stage separating the sync pulses from said video output signal;
  a pulse shaping stage to which the sync pulses from said pulse separating stage are supplied, said pulse shaping stage generating a trigger signal for said light source coinciding with the occurrence of each sync pulse;
  a strobe signal generator synchronizible to generate trigger signal for said light source at a frequency coinciding with the frequency of oscillation of said examination subject;
  a tone source for providing a synchronizing frequency to said strobe signal generator; and
  means connected to said light source and to said pulse shaping stage and said strobe signal generator for selectively connecting one of said pulse shaping stage or said strobe signal generator to said light source for triggering said light source.

22. An apparatus as claimed in claim 16, wherein said tone source is a tone generator having manually adjustable frequency control.

23. An apparatus as claimed in claim 16, wherein said tone source is a microphone arranged for picking up said oscillations of said examination subject, and further comprising a filter connected between said microphone and said strobe signal generator for filtering a selective frequency from the mix of frequencies obtained from said microphone for use as synchronizing frequency.

24. An apparatus as claimed in claim 21, wherein said light source is a strobe lamp.

* * * * *